United States Patent
Hardt

(10) Patent No.: US 8,340,753 B2
(45) Date of Patent: Dec. 25, 2012

(54) BINAURAL BEAT AUGMENTED BIOFEEDBACK SYSTEM

(76) Inventor: James V. Hardt, San Francisco, CA (US)

( * ) Notice: Subject to any disclaimer, the term of this patent is extended or adjusted under 35 U.S.C. 154(b) by 438 days.

(21) Appl. No.: 12/741,976

(22) PCT Filed: Nov. 14, 2008

(86) PCT No.: PCT/US2008/083686
§ 371 (c)(1),
(2), (4) Date: May 7, 2010

(87) PCT Pub. No.: WO2009/065076
PCT Pub. Date: May 22, 2009

(65) Prior Publication Data
US 2011/0105938 A1    May 5, 2011

Related U.S. Application Data

(60) Provisional application No. 60/988,764, filed on Nov. 16, 2007.

(51) Int. Cl.
*A61B 5/04*    (2006.01)

(52) U.S. Cl. .................................... 600/544; 600/545
(58) Field of Classification Search .................. 600/544, 600/545
See application file for complete search history.

(56) References Cited

U.S. PATENT DOCUMENTS

| | | |
|---|---|---|
| 4,334,545 A | 6/1982 | Shiga |
| 4,928,704 A | 5/1990 | Hardt |
| 5,036,858 A | 8/1991 | Carter |
| 5,356,368 A | 10/1994 | Monroe |
| RE36,348 E | 10/1999 | Carter |
| 6,081,743 A | 6/2000 | Carter |
| 2006/0030907 A1 | 2/2006 | McNew |
| 2006/0116597 A1 | 6/2006 | Vesely |
| 2006/0116598 A1 | 6/2006 | Vesely |
| 2006/0116600 A1 | 6/2006 | Vesely |
| 2006/0252978 A1 | 11/2006 | Vesely |
| 2006/0252979 A1 | 11/2006 | Vesely |

*Primary Examiner* — Navin Natnithithadha
*Assistant Examiner* — Etsub Berhanu
(74) *Attorney, Agent, or Firm* — Bert P. Krages, II

(57) ABSTRACT

A biofeedback system that incorporates binaural beat technology to augment the EEG feedback provided to the trainee. Specifically, the system will provide binaural beats at the frequency of the brain's naturally occurring peak energy in the EEG band or bands subject to the biofeedback.

15 Claims, 2 Drawing Sheets

US 8,340,753 B2

BINAURAL BEAT AUGMENTED BIOFEEDBACK SYSTEM

TECHNICAL FIELD

The invention relates generally to an apparatus and method for monitoring electroencephalography (EEG) activity for use in biofeedback training.

BACKGROUND ART

The invention is an improvement and extension of the EEG Biofeedback Method and System for Training Voluntary Control of Human EEG Activity as set forth in U.S. Pat. No. 4,928,704, which is fully incorporated by reference into this application. Biofeedback information can be used to foster rapid learning of self-control using electroencephalography (EEG). The invention covered in the '704 patent encompasses an EEG biofeedback apparatus for providing simultaneous, minimal phase delay feedback on multiple sub-bands of EEG filtered out of multiple independent EEG channels.

The most common purpose of biofeedback in general, and EEG biofeedback in particular, is to permit an individual to use the feedback information to learn a useful degree of voluntary self-control of a specific biofeedback parameter. Each of the major sub-bands of the EEG (alpha, beta, delta, gamma, theta) has unique bio-electric characteristics which correspond with unique subjective characteristics within the experience of the individual. Alpha is associated with a variety of wakeful states involving creativity, calming of the mind, and inner focus of awareness, beta is associated with alert wakeful situations with external focus as well as with stress and anxiety, delta is associated most clearly with coma and deep sleep, and theta is associated with light sleep and drowsiness. Gamma have not received as much attention from researchers but is associated with precognition and high-level information processing. Recently Buddhist meditators practicing "compassion meditation" showed big increases in Gamma EEG activity that were positively correlated with the number of 1,000s of hours of practice of this compassion meditation.

The use of simultaneous, minimal phase delay EEG biofeedback has been found to increase the likelihood of psychological benefits to trainees including enhanced serenity, deeper understandings, and relief from anxiety and depression. However, some trainees do not have much naturally-occurring activity (e.g., low amplitude and low abundance) in a particular brain wave band such as alpha or theta. This situation can present an impediment to the rate of improvement of self control experienced by such trainees. There is a need for a method that can enhance the biofeedback provided by the EEG biofeedback system in a way that instantaneously follows the brain's naturally-occurring frequencies of peak energy in a desired band or sub-band and that does not impose a peak energy at a non-naturally-occurring frequency. In addition, most trainees using prior art biofeedback systems benefit most when they focus attention on the one or two channels with the greatest amplitudes. In this context, the other weaker channels tend to follow along and do better than if the trainee has focused attention during the neurofeedback only on the weaker channels. Thus, there is also a need for a way to facilitate the ability for trainees to boost activity in weaker channels in a manner that avoids unnatural entrainment of brain wave frequency.

DISCLOSURE OF INVENTION

A primary benefit of the invention is that it facilitates learning self-control of one's own EEG activity through EEG biofeedback and by binaural-beat enhanced EEG biofeedback. It thus helps and enables trainees to learn control over their mental and emotional and spiritual subjective states and their underlying physiological states of their brain activity. The goal of such self-control is not confined to obtaining control of the measurable EEG parameters, but goes well beyond that to obtaining self-control of the mental and emotional and spiritual subjective states associated with the objectively measurable EEG sub-bands and sub-ranges.

The improvement and extension to the biofeedback system described in U.S. Pat. No. 4,928,704 is to incorporate binaural beat technology to augment the EEG feedback provided to the trainee. Specifically, the system will provide binaural beats at the frequency of the brain's naturally occurring peak energy in the EEG band or bands subject to the biofeedback. This frequency of peak energy changes dynamically and rapidly in the brains of most people so that the frequency at which the peak amplitude occurs in one instant may not be the frequency at which the peak amplitude occurs in the next instant. For example, alpha at 11 cycles per second could slow, within one cycle to become alpha at 8 cycles per second. This provision of binaural-beat augmented EEG feedback can be done for brain waves of any brain frequency band or range such as delta, theta, alpha, beta, or gamma. For example, the frequency range of alpha is 8-13 cycles per second and a person's alpha activity could be anywhere in that range. A person's alpha is not fixed at a stable frequency, and the frequency drifts and sometimes shifts suddenly, slowing and then speeding up again. In this invention, the EEG activity is analyzed to make a nearly instantaneous determination of the frequency at which the peak energy in the chosen feedback band, say for example the alpha band, is occurring. Any means suitable for analysis of the EEG signals could be used to determine this frequency of the instantaneous peak energy, examples include Fast Fourier Transforms (FFTs) or very narrow band digital filtering. As soon as the frequency having the maximum energy is determined, that frequency is used to determine the details of the binaural beat enhancement for augmenting the EEG biofeedback that is currently being provided to the trainee.

This EEG biofeedback system comprises either one or a pair of reference electrodes, a suitable ground electrode, and a plurality (number=N) of active cortical site electrodes that are placed on the head of a trainee (or client or Subject) with output signals directed to an equal number (N) of EEG amplifiers. The output of each of the active cortical site electrodes is filtered into sub-bands or sub-ranges of the EEG. The filtered signals can be converted into aural, visual, or tactile response indicia and supplied in real time to the trainee to allow the trainee to respond instantaneously to biofeedback signals. The system contemplates that at least 16 frequency sub-bands may be established: (1) slow delta, (2) fast delta, (3) broad band delta, (4) slow theta, (5) fast theta, (6) broad band theta, (7) slow alpha, (8) middle alpha, (9) fast alpha, (10) broad band alpha, (11) slow beta, (12) fast beta, (13) broad band beta, (14) slow gamma, (15) fast gamma, (16) broad band gamma. Frequency-domain filtering is accurately effected by the system with minimal delay and with great accuracy and precision, and additional narrower filter bands can be established to give finer resolution in the frequency domain. It is also possible to do Fast Fourier Transforms (FFTs) with very fine frequency resolution to give information on precisely which frequency within a band of interest (delta, theta, alpha, beta, or gamma) has the peak amplitude or peak energy at any given moment of time.

Whenever the frequency of the peak energy in the alpha (or other band or bands of interest) changes, then that new frequency is detected, analyzed, and used to determine the frequency that would receive binaural beat augmentation of the EEG feedback training currently underway. It is also possible to use the binaural beat enhanced EEG feedback in the spirit of this invention to augment frequencies other than that frequency at which the peak energy is occurring instantaneously. It may be that after some measurement period (a baseline) with or without EEG feedback, that a frequency can be identified, within the EEG band of interest, which, over time, has the greatest average energy or amplitude. This frequency could then be selected as the frequency to receive binaural beat enhancement to the neurofeedback process. In addition to this alternative method of determining the frequency to receive binaural beat enhancement to the biofeedback process there can also be other useful methods employed, such as selecting the frequency with the lowest detectable amount of energy or amplitude. This could be either the lowest average energy or the lowest detectable energy at any given moment. Statistical analysis of the energy distribution across the frequency band or range of interest could also be used to select frequencies for use in binaural beat augmentation of biofeedback, and these could include, but not be limited to, the centroid of the frequency x amplitude diagram, or the mean of, or the median of observed frequencies that are then weighted, or not, by amplitude, energy, or temporal abundance.

The process of binaural beat EEG entrainment occurs when two carrier tones of nearly identical frequencies are presented, one to each ear, and the brain detects a frequency difference between these two tones. When the two carrier tones are fed to a person via stereo headphones (or less ideally speakers very close to each ear), the brain will process the two signals and produce the sensation of a third sound called a binaural beat, which has a frequency equal to the difference in frequency between the two carrier tones. For example, a 300 Hz tone in one ear and a 310 Hz tone in the other ear produces a binaural beat at 10 Hz. Binaural beats can be detected by humans when the carrier tones are below approximately 1,000 cycles per second and can be readily generated at the low frequencies characteristic of the EEG spectrum (e.g.; less than 100 cycles per second).

Binaural beating has been associated with an EEG frequency entrainment response in the brain where its period of a particular brain wave will correspond to the fundamental frequency of the stimulus. In other words, providing carrier tones to induce the perception of binaural beating can result in entrainment in which brain wave activity is driven toward a predetermined state, i.e. the frequency at which the binaural beat is occurring. Thus, providing binaural beat frequencies to the brain can be a form of external control that can stimulate the production of brain waves that are not naturally occurring in the brain or at least not in that brain at that time. There might be some contraindications to doing this as may be suggested by Vivekananda in his 1931 book *Raja Yoga*. In this book Vivekananda writes ". . . it is better for a race to remain wicked than to be made artificially good through the morbid imposition of external control." (p. xx). Thus there may be ethical issues related to entrainment of brain wave activity, which would seem to be a form of "external control." However, by filtering the EEG signal to determine the frequency at which the person's the peak energy is occurring at each moment, the binaural beat frequency can be tailored to precisely follow, moment-by-moment, the brain's naturally occurring frequencies of peak energy, or other brain wave frequencies that exist within the brain, and thus can be used to enhance the biofeedback provided by the EEG biofeedback system. When used in this form, the augmentation provided by the binaural beat frequencies will not induce the production of brain waves that are not naturally occurring. This could thus be a more ethical (and a more effective) use of binaural beat technology in that it would be binaural beat augmented neurofeedback that may effectively avoid some of the issues of the type of interventions that Vivekananda warns against. All of the augmentation of EEG activity produced by the binaural beat process will be of EEG activity that is naturally occurring in the brain at that moment, or has occurred recently with detectable amplitudes. Indeed, the EEG activity that is being augmented by binaural beats in the preferred implementation is that EEG activity that is in each moment, the EEG activity of peak energy. This binaural beat methodology could be seen as more organic and more in harmony with the natural ecology of the brain's own naturally-occurring frequency patterns. This could mean that the binaural beat influence would be more effective, since the frequency(ies) being augmented by the binaural beat component of this invention is/are already a naturally occurring brain wave frequency or set of frequencies. It is easier for the brain to make more of some frequency(ies) that it is already producing than to start from scratch and to begin to make some frequency(ies) that is it not yet producing. This binaural-beat-augmented EEG feedback system enables the trainee to enhance the production of the desired and targeted brain wave activity by two processes simultaneously. The one process is the natural process of the brain responding to EEG feedback signals in one or more sensory modalities with the brain then increasing the amplitude and temporal abundance of the desired and targeted EEG frequency(ies), and the second process is the binaural beat augmentation of brain activity that occurs at the EEG frequency that is tracked and matched, in each moment, by the frequency or frequencies of the binaural beats. And the binaural beat frequencies are given only at the selected naturally occurring frequencies of the brain, such as, for example, the naturally occurring brain frequencies which have the peak energy in every moment. Binaural beat augmented biofeedback can thus be useful in various applications including those in which people who do not have much naturally-occurring activity (e.g. low amplitude and low abundance) in a particular brain wave band such as alpha or theta, and in teaching people with very large amplitudes of desirable brain wave patterns to develop even larger amplitudes and greater abundances of their most desirable brain wave patterns.

The preferred means of providing binaural-beat-augmented EEG biofeedback is by producing two tones in the respective sides of a set of stereo headphones worn by a trainee. However, any arrangement in which a speaker is located close to each ear could be used. The main feedback tone for the auditory EEG biofeedback at a given head site or set of head sites would be one of the two tones that would be provided to one side of the stereo headset. This main tone is amplitude modulated to track the envelope of the EEG activity, which is the target or the trainee of the EEG feedback. On one side only of the stereo headset, this main feedback tone would be suitably amplitude modulated to proportionally track the envelope of one of the types of filtered EEG activity that is the training target of the EEG feedback. The frequency of the tone would be ideally under 1,000 Hz. The other tone that would provide the second frequency needed to provide the binaural beat entrainment of the trainee's peak alpha frequency (or other frequency of choice), would be delivered only to the other side of the stereo headset and it can be of a much lower volume and it need not be related to the amplitude of the ongoing EEG activity. This second tone could be quite unobtrusive (very quiet) and yet still participate effectively in the entrainment of the person's frequency of peak amplitude or other some other frequency of a desired brain wave pattern. In general, a loud secondary tone will not aid in the perception by the trainee and can become a major distraction from the main feedback tone. Although there are no technical difficulties associated with having the secondary tone loud or louder than the primary tone, such a scenario could detract from the biofeedback process because the secondary tone is not involved in the EEG amplitude and/or EEG frequency variations that are the core of the neurofeedback process as contemplated by the preferred embodiment. Also if the secondary tone were too loud, then its frequency variations might become noticeable and become annoying, in an analogous manner to a musical piece that had one instrument that slides into being sharp and then flat and then sharp and the flat more or less continually.

This process of binaural-beat-augmented EEG feedback could be done on just one of the EEG channels (and thus just one of one set of the head sites) of the EEG feedback process and that channel could be the channel with the greatest amplitude or the lowest amplitude or any other channel or combinations of channels of interest. The process could also be done on a plurality of channels simultaneously, since the EEG biofeedback system can function using multiple independent channels simultaneously. The EEG biofeedback system can also be productively used to boost the weakest one or two channels of a multi-channel montage. When used in this manner, strategies of training can be selected that are related to the initial ranking of the amplitudes of each channel and thus facilitate emphasis on working with the channels having largest or the smallest amplitude. However, the present invention would also make it possible to select intermediate channels based on predetermined parameters such as rate of brain wave amplitude and/or frequency fluctuation, and the like. Note that while the EEG biofeedback system encompasses the ability to simultaneously monitor and to provide EEG feedback on multiple channels, the binaural beat augmentation contemplated by this improvement could also be used in a single channel device and that this invention encompasses both single-channel and multiple channel embodiments.

In the preferred embodiment of the system, the main feedback tone is set at a specific tone frequency and then the brain wave frequency is monitored and processed to determine the frequency of the secondary tone such that the difference between the main and secondary tone frequencies equals, in one preferred embodiment, the brain wave frequency of peak energy at each moment. The user perceives a main tone (the feedback tone) to be of constant frequency and the volume of the main (feedback) tone varies depending on the amplitude of the brain wave within the selected frequency band, i.e., the entire alpha band or some sub-band within the alpha band. However, other embodiments can be practiced such as having the frequency of the main tone be determined by brain wave frequency such that the frequency of the main tone shifts concurrently with a shift in the brain wave frequency. This would produce a different perception by the user but could nonetheless be used as a means of providing feedback. Many people have observed that varying the pitch of the main biofeedback tone is highly distracting and unpleasant. Noticeable frequency changes tend to cause hyper-alerting responses which are incompatible with the calming and steadying of the arousal level that is the most common objective of EEG biofeedback training. However, the ability to provide biofeedback in modes in which the frequency of the main tone shifts could be desirable in certain situations such as behavioral research and is thus encompassed by the invention.

Similarly, the system could be keyed off of some fraction of a brain wave band or sub-band other than the part associated with the peak energy. For example, the average or median energy could be used. While the preferred embodiment is based on selection based on the peak energy to avoid substantial interference with the naturally-established brain wave patterns of trainees, other embodiments could make selections based on non-peak energy levels albeit with some possible risk to the trainee caused by disruption to their normal, pre-existing brain wave patterns.

It should also be noted that the signals used to determine the tones that are used to produce the audio feedback of the EEG activity can also be processed electronically to provide feedback in forms in addition to audio. For example, the signals could be processed to produce a visual stimulus or graphic reflecting the biofeedback or to produce a tactile output through means such as a vibration device. Such variations could be used alone or in conjunction with the audio feedback tones to motivate and accelerate learning of EEG self-regulation and self-control.

The method of using the system is readily discernable from the description above and the incorporated reference patent. In any case, one of the basic forms of the method comprises the following steps:
  (a) placing EEG sensors on cortical sites on the head of a person;
  (b) sensing electric potentials from the cortical sites to obtain a signal for a selected brainwave;
  (c) processing the signal to determine the frequency of the peak energy of the signal or other relevant aspects of the signal according to a training program;
  (d) using the frequency of the peak EEG energy to determine the frequency of a tone secondary to a main tone; and
  (e) monitoring the brain wave signal and processing on a continuing basis to instantaneously provide the audio feedback to the person to indicate to the person the EEG activity at the cortical sites in order to facilitate voluntary conscious and unconscious control over said personal EEG activity.

MODES FOR CARRYING OUT THE INVENTION

The preferred embodiment is directed at a method of using binaural beat enhanced biofeedback to assist a trainee in focusing on the frequency in which the peak energy of a selected band, such as alpha, is naturally occurring. However, the preferred embodiment also provides means of providing biofeedback to a trainee with respect to other ranges of brainwave frequencies.

Figure 1:
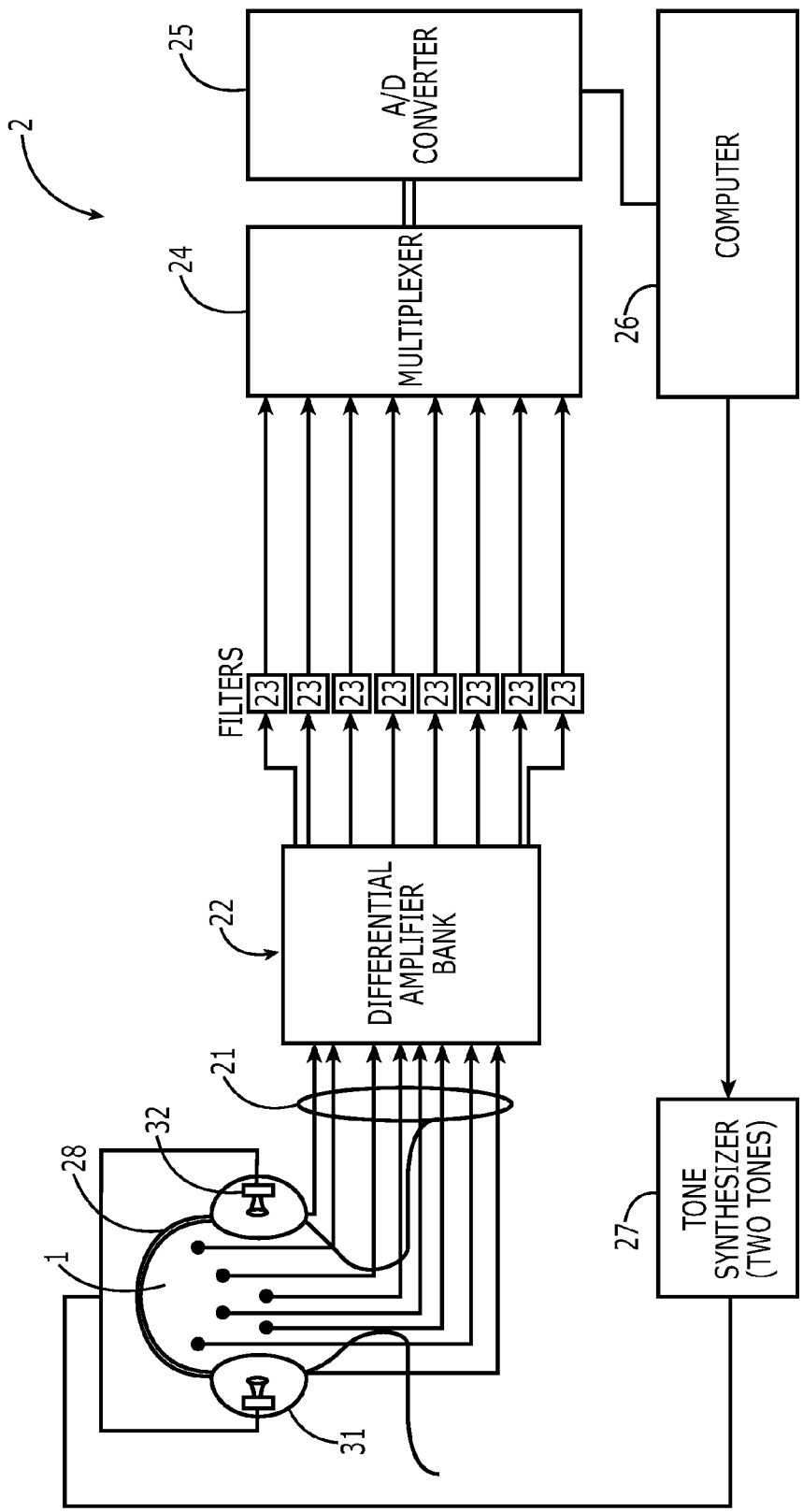
FIG. 1 is a diagram showing the trainee and the biofeedback apparatus.

Referring to FIG. 1, The trainee 1 is connected to provide input to the apparatus 2 through EEG leads 21 and to receive audio output from the apparatus 2 through stereo headphones 28. On the head of the trainee 1 are mounted a plurality of EEG leads 21 including a pair of reference electrodes attached to the ear lobes, a suitable ground electrode, and a plurality of active cortical site electrodes mounted in lateral pairs and used in monopolar configuration. The output signals directed to an equal number of EEG amplifiers in an EEG amplifier bank 22. The output of each of the active cortical site electrodes is amplified and filtered into sub-bands or sub-ranges of the EEG in a corresponding number of multiple channel filter banks 23, and thereafter through a multiplexer 24 to a analog-to-digital converter 25. It is preferred to use high input impedance, low noise, low drift operational amplifiers, low current drain amplifiers to permit optional use with battery power sources. Elimination of line voltage power increases common mode rejection by eliminating all coupling to the 60 Hz AC line. In the preferred embodiment, the EEG amplifier bank 23 contains analog bandpass filters in sets of eight. The bandpass filters according to the invention may be active and are characterized by an elliptical response with 300-400 dB per octave rolloff at the skirts, 0.25 dB ripple in the pass-band and at least 50 dB rejection in the stop band. The filters have a pass-band of only a few Hertz. The filter sets spectrally decompose the EEG signals through its input from an electrode into a plurality of sub-bands. The sub-bands may be chosen according to the training level of the trainee and object of the training. In the preferred embodiment, the filters are configured to select the specific sub-bands: delta (2.0-3.5 Hz), slow theta (4.2-5.4 Hz), fast theta (5.5-6.8 Hz), slow alpha (7.5-8.8 Hz), broadband alpha (7.7-12.6 Hz), fast alpha (10.8-12.9 Hz), slow beta (14.2-17.2 Hz), and broadband beta (1 5.0-24.0 Hz). Alternative bands or sub-bands may be designated, such as broadband theta (4.0-6.7 Hz), middle alpha (8.9-10.7 Hz), and fast beta (17.3-24.0 Hz). Under selected conditions, only a few of the sub-bands are processed and made available as feedback signals. The outputs of each filter set may be made available as (a) filtered EEG, (b) filtered, full-wave rectified EEG, and (c) filtered, full-wave rectified and smoothed EEG. The outputs are fed into a multiple-channel multiplexer 24. The multiplexer 24 in turn directs the signals as analog samples to the 12-bit analog-to-digital converter 25. In this embodiment, a microcomputer 26 is provided for real-time processing of the output digital samples although such processing could alternatively be done by a mainframe computer or one or more dedicated microprocessors. Note that the microcomputer 26 encompasses the typical devices associated with microcomputers such as a keyboard and mouse input devices, one or more monitors, one or more printers, memory, and a central processing unit. The microcomputer 26 serves a variety of control and data recording functions and the peripherals provide conventional input and output functions in support of the control and analysis functions of the microcomputer 26. One such function of the microcomputer 26 is to evaluate the digital signals to determine the amplitude of the peak energy within the selected band or sub-band and the frequency at which that peak energy occurs. Digital processing software such as those using a fast Fourier transform (FFT) algorithm can be run on the microcomputer 26 to implement this function. The peak energy frequency is used to set the frequency of the binaural beat enhancement of the neurofeedback. As the frequency changes, it becomes the new frequency used to set binaural beat enhancement.

The microcomputer sends a signal representative of the amplitude and frequency of the peak energy within the desired band or sub-band to a tone synthesizer 27. The purpose of the tone synthesizer 27 is to create two signals via two channels, one of which is sent to speaker 31 and the other which is sent to speaker 32. Preferably, these speakers are mounted in stereo headphones 28 that are worn by the trainee 1. In the preferred embodiment, the tone synthesizer 27 generates a signal in the first channel that is set a constant frequency and whose amplitude varies in proportion to the peak energy occurring within the desired band or sub-band. The tone synthesizer 27 simultaneously generates a signal in the second channel at a constant amplitude which is set substantially lower than the amplitude of the signal in the first channel and at a frequency which is lower than the frequency of the signal of the first channel by the frequency at the which the peak energy is occurring within the desired band or sub-band. For example, consider a trainee session at which the signal generated in the first channel of the tone synthesizer corresponds to 450 Hz. If the desired band monitored in the trainee 1 is broadband alpha (7.7-12.6 Hz), and frequency of the peak energy at one moment in time is measured to be 10 Hz, the signal in the second channel would be generated to correspond to a frequency of 440 Hz (i.e., 450Hz -10 Hz). If the frequency of the peak energy at a short time later is measured at 12 Hz, the signal in the second channel would be generated to correspond to a frequency 438 Hz. (i.e., 450Hz -12 Hz). The tone synthesizer can encompass any of the well-established means of operation including analog, digital, software-based, and hybrids thereof.

Tones are the principal mechanism for real-time feedback employed for EEG training in accordance with the invention. Tones as perceived at the speakers 31 and 32 must be maintained at substantial volume and duration for rapid learning of self control by the trainee. Tone quality is also critical to learning control. For example, tone onset causes blocking (abolition or diminution) of EEG alpha as a nonlinear function of tone frequency. Blocking duration is minimal between about 400 Hz and 800 Hz and that above and below these frequencies, blocking duration rises rapidly. If tone onset occurs in response (feedback) to alpha onset and if tone onset causes alpha blocking, then the result is negative feedback and is thus unlikely to promote learning of alpha EEG control. According to the invention therefore, the tones are chosen to lie only between about 400 Hz and 800 Hz for alpha training. According to the invention therefore, the tones are chosen to lie only between about 400 Hz and 800 Hz for alpha and beta training. In theta training, however, a principal problem is drowsiness with the trainee falling asleep, so a higher pitched more piercing tone is appropriate for theta training. This also allows non-overlap between the alpha tones (about 400-800 Hz) and theta feedback tones (above about 800 Hz).

The waveform of the tone is also important to learning. It is easy to generate square waves and sawtooth waves electronically, but they have an unpleasant quality with abundant harmonics generated at the leading and trailing edges. Square waves are difficult to listen to at the high volume and for the long periods of time which are important for successful and rapid learning of EEG self control. Preferably one should use: (a) pure sine waves generated electronically and amplitude modulated or (b) pure notes representing the tones made by a trainee's preferred musical instrument. The essential purpose here is to have the tones pleasing to listen to for long periods of time at loud and varying volumes, with a selection of tone frequencies designed to prevent or minimize negative feedback (reduction of EEG signal to tone onset).

The amplitude of the tone feedback should be linearly related to the amplitude of the instantaneous filtered EEG. The dynamic range of the system must be capable of reflecting the full range of BEG variations. However, this linear relationship does not mean that tone volume should go to zero when the feedback signal goes to zero amplitude. It is disruptive to learning to have the feedback tones shut off completely and then turned on, possibly suddenly. As a result there should be an audio offset, in which the volume of the tone generated from the first channel of the tone synthesizer 27 is never less than the volume of the tone generated in the second channel of the tone synthesizer 27. This continuity of sound facilitates learning and minimizes the disrupting effects of tone onset.

It is highly desirable to minimize the delay between the sensing of an EEG event and the presentation of that event to the trainee in the form of a tone. According to the invention, the feedback delay should be less than about 350 ms and preferably less than 200 ms to optimize feedback training. In the preferred embodiment the feedback delay is less than 100 ms, which is less than one alpha wave cycle.

Figure 2:
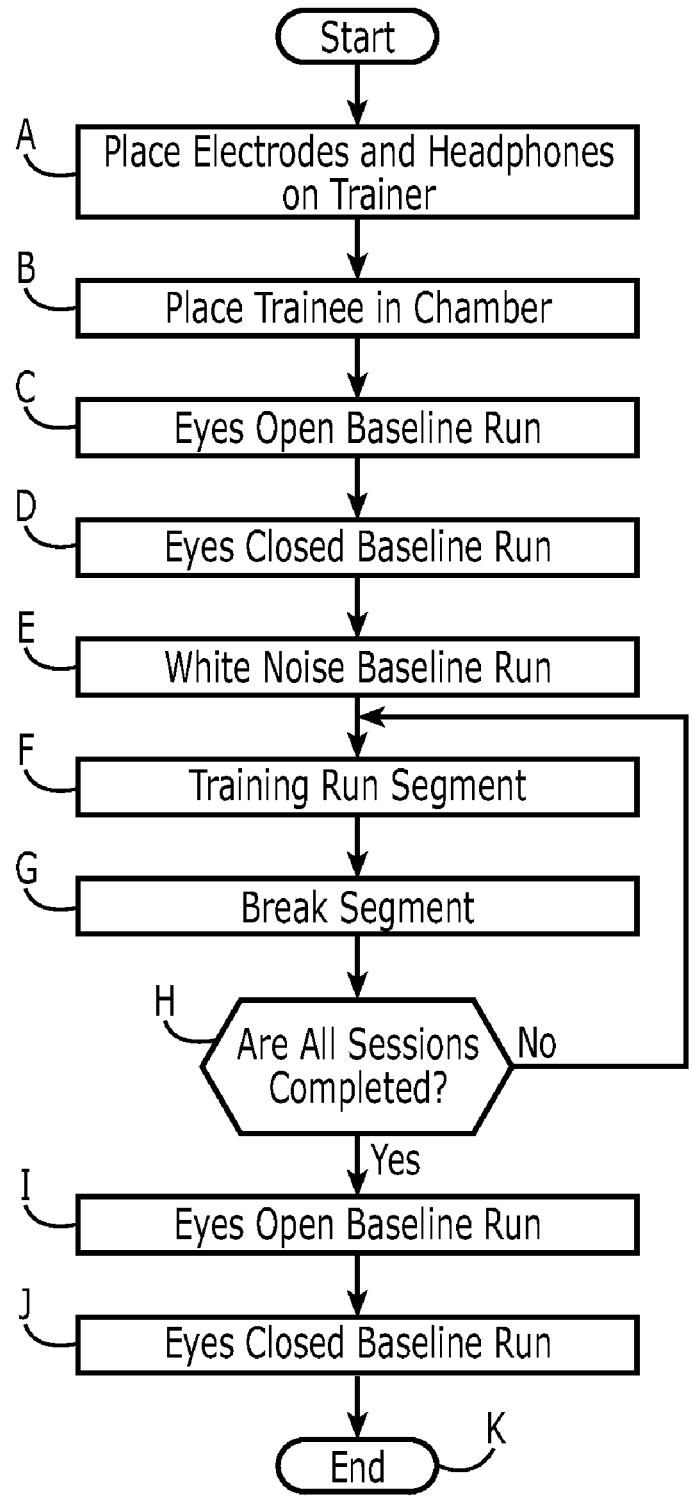
FIG. 2 is a block diagram showing the method according to the preferred embodiment of the present invention.

Referring to FIG. 2, a preferred embodiment of the method according to the invention is presented. The method implements a training regimen to enable an individual to train for increased amplitude of EEG at the naturally-occurring peak energy of a desired band or sub-band.

First, the array of EEG leads is emplaced at the selected cortical sites of the trainee (Step A). There is provided a ground and two references, as well as carefully-sited active electrodes, typically placed in laterally-symmetric pairs in order to sense surface brain potentials representative of brainwave signals to be subjected to training The trainee is then placed in the training chamber used for feedback training, preferably darkened sound-proof room with a comfortable chair, and the electrodes are connected to the EEG apparatus and the stereo headphones are placed over the trainee's ears. (Step B).

Baseline testing is then generally conducted. An "eyes open" baseline is then run which is designed to reveal the trainee's minimal alpha levels and to allow the operator to check out and calibrate all instruments. (Step C). The "eyes open" baseline run is generally in the presence of bright light and with a steady background tone in both speakers set to the frequency of tone that will be created in the first channel of the tone synthesizer. During the run, the trainee is instructed to focus on a specific object in the field of view. If desired, adjustments can be made to the volume of the tones in order to make the training comfortable for the trainee. The data is collected with respect to the amplitude and energy frequencies of the brainwave activity and stored into the memory of the microcomputer. An "eyes closed" baseline is then run to determine the nature of brainwave activity in the absence of conventional stimuli (Step D). This is conducted in darkness with a steady background tone in both speakers set to the frequency of tone that will be created in the first channel of the tone synthesizer. The data is collected with respect to the amplitude and energy frequencies of the brainwave activity and stored into the memory of the microcomputer. A "white noise" baseline is then run in preparation for the actual training sessions or epochs (Step E). The white noise run is used to condition the trainee to attend to an auditory signal while allowing the mind to relax without loss of recollection ability. White or quasi-white Gaussian noise is provided by speakers of the stereo headphones. Data is collected with respect to the amplitude and energy frequencies of the brainwave activity and stored into the memory of the microcomputer.

The training session consists of two segments that may be repeated several times. The biofeedback segment is conducted for a period of about 120 seconds (Step F). A break segment of about eight seconds occurs after each biofeedback segment (Step G). The standard biofeedback segment consists of feedback of tones into the stereo headphones. As described previously, the tone from one speaker is set at a constant frequency within the range of 400-800 Hz and the volume varies in proportion to the amplitude of the brain waves being monitored within the selected frequency band. The tone from the other speaker is set at a constant volume much lower that the volume levels of the first speaker and is set at a frequency which is lower than the frequency of the signal of the first channel by the frequency at the which the peak energy is occurring within the desired band or subband.

During the break segment, the audio feedback is suppressed. If desired, the trainee 1 may be presented with discrete scores are presented for each active EEG lead or selected combination of EEG leads summarizing immediate past performance according to the amplitude integral over the prior measurement period. Presentation of this discrete scoring information may presented visually by means such as a digital readout or aurally by means such as a digital speech synthesizer. The training session is then generally repeated several times until the desired number of training sessions have been completed (Step H).

Once the desired number of training sessions have been completed, more baselines are run, namely, eyes open baseline (Step I), and an eyes open baseline (Step J). The stereo headphones and EEG leads are removed from the trainer and the regimen is brought to an end (Step K). In addition, the step of a running a white noise baseline could be done (not shown) immediately after the session are completed (step H) and the order in which the eyes open baseline run (step J) and the eyes closed baseline run (step K) could be reversed. The operator may analyze the data collected during the sessions and interview the trainee to reinforce any brainwave control which has been demonstrated. Interviews are important because the trainee is required to verbalize his reaction strategies, which reinforces memory of the strategies for future training.

As will be apparent to a person skilled in the art, a number of variations and modifications can be made to the system and method described above without departing from the spirit and scope of the present invention. All such modifications and variations are contemplated as being within the scope of the invention.

I claim:

1. A method for training a person to develop useful degrees of voluntary control of personal electroencephalographic (EEG) activity, said method comprising the steps of:
   (a) securing EEG leads to the person;
   (b) receiving an EEG signal from the person;
   (c) transmitting the resultant EEG signal to a filter;
   (d) filtering the EEG signal; and
   using a computing device:
   (e) monitoring a predetermined EEG frequency band or subband;
   (f) determining an EEG frequency value of a preselected aspect of said EEG signal; and
   (g) generating a first audio signal at a first frequency that is delivered to said person's first ear with minimal delay and generating a second audio signal that is delivered to said person's second ear concurrently with said first audio signal, said second audio signal having a second frequency that differs from said first frequency by the value of said EEG frequency value;
   wherein said preselected aspect is the frequency at which the peak energy of the EEG signal occurs.

2. The method of claim 1 wherein the frequency of the first audio signal is constant and the volume of first audio signal varies in proportion with the amplitude of said EEG signal.

3. The method according to claim 1 wherein said first audio signal tone is between about 400 Hz and about 800 Hz as a representative signal for alpha training.

4. The method according to claim 1 wherein said first audio signal has a tone above about 800 Hz as a representative signal for theta training.

5. The method of claim 1 wherein said minimal delay is less than 350 MS.

6. A method for training a person to develop useful degrees of voluntary control of personal electroencephalographic (EEG) activity, said method comprising the steps of:
(a) securing EEG leads to the person;
(b) receiving an EEG signal from the person;
(c) transmitting the resultant EEG signal to a filter;
(d) filtering the EEG signal; and
using a computing device:
(e) monitoring a predetermined EEG frequency band or subband;
(f) determining an EEG frequency value of a preselected aspect of said EEG signal; and
g) generating a first audio signal at a first frequency that is delivered to said person's first ear with minimal delay and generating a second audio signal that is delivered to said person's second ear concurrently with said first audio signal, said second audio signal having a second frequency that differs from said first frequency by the value of said EEG frequency value;
wherein said preslected aspect is the frequency at which the greatest average energy of the EEG signal occurs over a pre-selected interval of time.

7. The method of claim 6 wherein the frequency of the first audio signal is constant and the volume of first audio signal varies in proportion with the amplitude of said EEG signal.

8. A method for training a person to develop useful degrees of voluntary control of personal electroencephalographic (EEG) activity, said method comprising the steps of:
(a) securing EEG leads to the person;
(b) receiving an EEG signal from the person;
(c) transmitting the resultant EEG signal to a filter;
(d) filtering the EEG signal; and
using a computing device:
(e) monitoring a predetermined EEG frequency band or subband;
(f) determining an EEG frequency value of a preselected aspect of said EEG signal; and
(g) generating a first audio signal at a first frequency that is delivered to said person's first ear with minimal delay and generating a second audio signal that is delivered to said person's second ear concurrently with said first audio signal, said second audio signal having a second frequency that differs from said first frequency by the value of said EEG frequency value;
wherein said pre-selected aspect is the frequency at which the lowest detectable energy of the EEG signal occurs over a preselected interval of time.

9. The method of claim 8 wherein the frequency of the first audio signal is constant, and the volume of first audio signal varies in proportion with the amplitude of said EEG signal.

10. An apparatus for training a person to develop useful degrees of voluntary control of personal electroencephalographic (EEG) activity, said apparatus comprising:
(a) a plurality of EEG sensors, said sensors being for placement at a plurality of cortical sites on a head of said person;
(b) amplifiers coupled to said EEG sensors to amplify a plurality of channel signals in a plurality of channels;
(c) a plurality of bandpass filters coupled to said amplifiers having a passband characteristic of a predefined frequency spectra having an abrupt cutoff at a low-frequency skirt, an abrupt cutoff at a high-frequency skirt and near instantaneous propagation for processing in accordance within time constraints limited by natural neurological reactivity to obtain a resultant EEG signal for each said channel;
(d) a computing device to perform the operation of determining an EEG frequency value based on a preselected aspect of one or more of the resultant signals; and
(e) a tone synthesizer receiving input from said computing device and generating a first audio signal at a first frequency that is delivered to said person's first ear and generating a second audio signal that is delivered to said person's second ear, said second audio signal having a second frequency that differs from said first frequency by the value of said EEG frequency value; wherein said preselected aspect is the frequency at which the peak energy of the EEG signal occurs.

11. The apparatus of claim 10 wherein the frequency of the first audio signal is constant and the volume of first audio signal varies in proportion with the amplitude of said EEG signal.

12. An apparatus for training a person to develop useful degrees of voluntary control of personal electroencephalographic (EEG) activity, said apparatus comprising:
(a) a plurality of EEG sensors, said sensors being for placement at a plurality of cortical sites on a head of said person;
(b) amplifiers coupled to said EEG sensors to amplify a plurality of channel signals in a plurality of channels;
(c) a plurality of bandpass filters coupled to said amplifiers having a passband characteristic of a predefined frequency spectra having an abrupt cutoff at a low-frequency skirt, an abrupt cutoff at a high-frequency skirt and near instantaneous propagation for processing in accordance within time constraints limited by natural neurological reactivity to obtain a resultant EEG signal for each said channel;
(d) a computing device to perform the operation of determining an EEG frequency value based on a preselected aspect of one or more of the resultant signals; and
(e) a tone synthesizer receiving input from said computing device and generating a first audio signal at a first frequency that is delivered to said person's first ear and generating a second audio signal that is delivered to said person's second ear, said second audio signal having a second frequency that differs from said first frequency by the value of said EEG frequency value; wherein said preselected aspect is the frequency at which the greatest average energy of the EEG signal occurs over a preselected interval of time.

13. The apparatus of claim 12 wherein the frequency of the first audio signal is constant and the volume of first audio signal varies in proportion with the amplitude of said EEG signal.

14. An apparatus for training a person to develop useful degrees of voluntary control of personal electroencephalographic (EEG) activity, said apparatus comprising:
(a) a plurality of EEG sensors, said sensors being for placement at a plurality of cortical sites on a head of said person;
(b) amplifiers coupled to said EEG sensors to amplify a plurality of channel signals in a plurality of channels;
(c) a plurality of bandpass filters coupled to said amplifiers having a passband characteristic of a predefined frequency spectra having an abrupt cutoff at a low-frequency skirt, an abrupt cutoff at a high-frequency skirt and near instantaneous propagation for processing in accordance within time constraints limited by natural neurological reactivity to obtain a resultant EEG signal for each said channel;

(d) a computing device to perform the operation of determining an EEG frequency value based on a preselected aspect of one or more of the resultant signals; and (e) a tone synthesizer receiving input from said computing device and generating a first audio signal at a first frequency that is delivered to said person's first ear and generating a second audio signal that is delivered to said person's second ear, said second audio signal having a second frequency that differs from said first frequency by the value of said EEG frequency value; wherein said preselected aspect is the frequency at which the lowest detectable energy of the EEG signal occurs over a preselected interval of time.

15. The apparatus of claim 14 wherein the frequency of the first audio signal is constant and the volume of first audio signal varies in proportion with the amplitude of said EEG signal.

* * * * *